(12) United States Patent
Augustine et al.

(10) Patent No.: US 6,248,084 B1
(45) Date of Patent: Jun. 19, 2001

(54) WOUND TREATMENT DEVICE

(75) Inventors: Scott D. Augustine, Bloomington; Randall C. Arnold, Minnetonka; Donald E. Stapf, Minneapolis; Gregory P. Hamlin, St. Paul, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/434,411

(22) Filed: Nov. 4, 1999

Related U.S. Application Data

(63) Continuation of application No. 08/965,588, filed on Nov. 6, 1997, now Pat. No. 6,010,527, which is a continuation of application No. 08/342,741, filed on Nov. 21, 1994, now Pat. No. 5,817,145.

(51) Int. Cl.$^7$ ...................................................... A61F 7/00
(52) U.S. Cl. .................................. 602/2; 602/14; 602/42; 607/96; 607/114
(58) Field of Search .................................. 602/2, 14, 41, 602/42, 47, 52, 54, 57; 607/96, 108, 114

(56) References Cited

U.S. PATENT DOCUMENTS

| | | |
|---|---|---|
| 222,690 | 12/1879 | Goldschmidt . |
| 697,637 | 4/1902 | Lee . |
| 720,812 | 2/1903 | Johnson . |
| 1,384,467 | 7/1921 | Homan . |
| 1,399,095 | 12/1921 | Webb, Sr. . |
| 1,777,982 | 10/1930 | Popp . |
| 1,920,808 | 8/1933 | Sander ................................ 128/154 |
| 1,979,082 | 10/1934 | Schwedenberg et al. ............. 219/46 |
| 2,221,758 | 11/1940 | Elmquist ............................. 128/154 |
| 2,443,481 | 6/1948 | Sene .................................... 128/155 |
| 2,573,791 | 11/1951 | Howells .............................. 128/82.1 |
| 2,577,945 | 12/1951 | Atherton ............................. 128/156 |
| 2,599,523 | 6/1952 | Dorr .................................... 128/153 |
| 2,601,189 | 6/1952 | Wales, Jr. ............................... 4/160 |
| 2,632,443 | 3/1953 | Lesher ................................. 128/156 |
| 2,706,988 | 4/1955 | Weber ................................. 128/102 |
| 2,769,892 | * 11/1956 | Collins ................................ 607/111 |
| 3,026,974 | 3/1962 | Stevens .............................. 128/260 |
| 3,528,416 | 9/1970 | Chamberlain ...................... 128/154 |

(List continued on next page.)

FOREIGN PATENT DOCUMENTS

| | | | |
|---|---|---|---|
| 269938 | 7/1950 | (CH) . | |
| 0269938 | * 11/1950 | (CH) | ................................... 607/96 |
| 378465 | 7/1964 | (CH) . | |
| 31 02 674 | 9/1982 | (DE) . | |
| 31 18 232 | 11/1982 | (DE) . | |
| 35 39 533 | 5/1987 | (DE) . | |
| 0 424 165 A1 | 10/1990 | (EP) . | |
| 0 485 657 | 5/1992 | (EP) . | |
| 0607472 | * 1/1993 | (EP) | ................................... 607/96 |
| 1303238 | 9/1961 | (FR) . | |
| 1 489 127 | 7/1967 | (FR) . | |
| 1 527 887 | 4/1968 | (FR) . | |
| 1527887 | 4/1968 | (FR) . | |
| 1527887 | 6/1968 | (FR) . | |
| 2 544 202 | 10/1984 | (FR) . | |
| 3090 | 6/1902 | (GB) . | |
| 288220 | 7/1927 | (GB) . | |
| 2 082 919 | 3/1982 | (GB) . | |
| 2 199 501 | 7/1988 | (GB) . | |
| 2261822 | 6/1993 | (GB) . | |
| 89/04158 | 5/1989 | (WO) . | |
| 94.00090 | 1/1994 | (WO) . | |
| WO 96 15745 | 5/1996 | (WO) . | |

*Primary Examiner*—Robert L. Nasser
(74) *Attorney, Agent, or Firm*—Gray Cary

(57) ABSTRACT

A non-contact wound treatment device having a flexible portion to accommodate patient motion without peeling off. A removable wound heater may be used to treat the wound area.

12 Claims, 8 Drawing Sheets

U.S. PATENT DOCUMENTS

| | | | |
|---|---|---|---|
| 3,596,657 | 8/1971 | Eidus | 128/156 |
| 3,610,238 | 10/1971 | Rich, Jr. | 128/184 |
| 3,610,251 | 10/1971 | Sanderson | 128/379 |
| 3,687,143 | 8/1972 | Schneeberger et al. | 128/402 |
| 3,691,646 | 9/1972 | Ruffolo | 34/90 |
| 3,782,377 | 1/1974 | Rychlik | 128/132 |
| 3,814,095 | 6/1974 | Lubens | 128/260 |
| 3,867,939 | 2/1975 | Moore | 128/254 |
| 3,881,477 | 5/1975 | Von Otto | 128/132 |
| 4,080,971 * | 3/1978 | Leeper | 601/111 |
| 4,134,399 | 1/1979 | Halderson . | |
| 4,172,495 | 10/1979 | Zebuhr et al. | 165/46 |
| 4,279,255 | 7/1981 | Hoffman | 128/402 |
| 4,341,209 | 7/1982 | Schaar | 128/156 |
| 4,382,441 | 5/1983 | Svedman | 604/291 |
| 4,399,816 | 8/1983 | Spangler | 128/154 |
| 4,484,574 | 11/1984 | DeRusha et al. | 128/156 |
| 4,517,972 | 5/1985 | Finch, Jr. | 128/156 |
| 4,540,412 | 9/1985 | Van Overloop | 604/128 |
| 4,572,188 | 2/1986 | Augustine et al. | 128/380 |
| 4,628,930 | 12/1986 | Williams . | |
| 4,633,863 | 1/1987 | Filips et al. | 128/165 |
| 4,641,641 | 2/1987 | Strock | 128/132 |
| 4,641,643 | 2/1987 | Greer | 128/156 |
| 4,667,666 | 5/1987 | Fryslie | 128/156 |
| 4,890,608 | 1/1990 | Steer | 128/156 |
| 4,962,761 | 10/1990 | Golden | 128/400 |
| 4,969,881 | 11/1990 | Viesturs | 604/305 |
| 5,003,971 | 4/1991 | Buckley | 128/156 |
| 5,025,777 | 6/1991 | Hardwick | 126/263 |
| 5,060,662 | 10/1991 | Farnswoth, III . | |
| 5,086,763 | 2/1992 | Hathman . | |
| 5,107,832 | 4/1992 | Guibert et al. | 128/399 |
| 5,135,518 * | 8/1992 | Verg | 602/41 |
| 5,144,113 | 9/1992 | Hall et al. | 219/549 |
| 5,144,958 | 9/1992 | Krueger et al. | 128/743 |
| 5,170,781 | 12/1992 | Loomis | 128/118.1 |
| 5,190,031 | 3/1993 | Guibert et al. | 128/399 |
| 5,230,350 | 7/1993 | Fentress | 128/846 |
| 5,431,622 * | 7/1995 | Pxrozyk et al. | 607/96 |
| 5,531,670 * | 7/1996 | Westby | 602/58 |
| 5,609,619 | 3/1997 | Pompei | 607/104 |
| 5,662,624 | 9/1997 | Sundström et al. | 604/291 |
| 5,817,145 * | 10/1998 | Augustine et al. | 607/96 |

\* cited by examiner

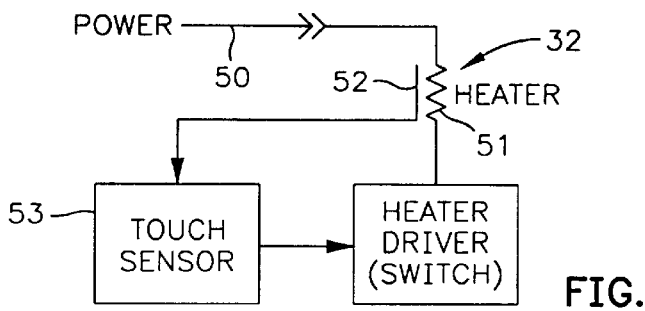
FIG. 8
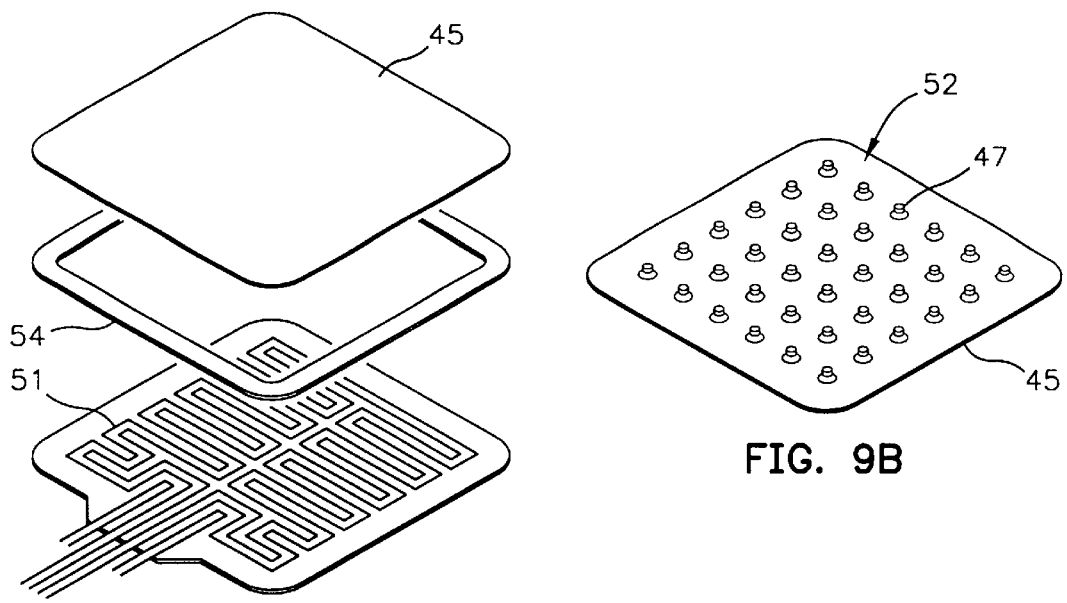
FIG. 9A
FIG. 9B
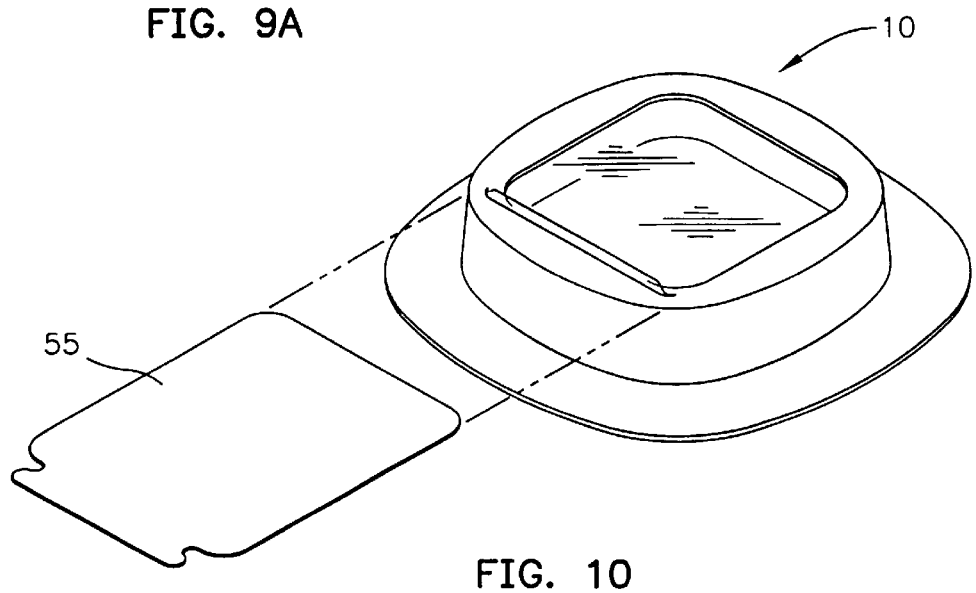
FIG. 10

WOUND TREATMENT DEVICE

This is a continuation application of U.S. patent application Ser. No. 08/965,588, filed Nov. 6, 1997, now U.S. Pat. No. 6,010,527, which is a continuation of U.S. patent application Ser. No. 08/342,741, filed Nov. 21, 1994, now U.S. Pat. No. 5,817,145.

TECHNICAL FIELD

The invention relates to a wound treatment device for covering and in some applications heating skin lesions; surgical wounds and the like. The wound treatment device includes a wound cover which can support a detachable planar wound heater. The wound covering provides a non-contact wound treatment volume over the wound area. The planar heater supplies or reflects heat from the wound area. The invention also relates to and addresses methods for making the wound covering and to methods for treating a wound.

BACKGROUND OF THE INVENTION

One traditional method of treating a wound involves the placement of a sterile gauze over the wound area and holding the gauze in place with adhesive tape. This type of wound dressing has numerous shortcomings. The wound is not fully isolated from the environment and can exchange bacteria with the environment. The gauze can adhere to the wound area interfering with the healing process which is undesirable as well. This traditional form of bandage does not control the thermal environment of the wound and this is undesirable as well.

Although wound heaters and non-contact wound coverings are known they are not generally accepted for several reasons. Wound coverings which include a rigid enclosure forming a cavity that covers the wound are usually adhesively attached to the skin of the patient with a relatively inelastic material. This results in the inability of the wound covering to accommodate patient motion. Usually patient motion will cause the rigid wound covering to peel-off of the patient's skin. The traditional solution to this problem has been to use a more aggressive adhesive tape or the like to more firmly attach the wound covering to the skin. This solution to the problem results in an uncomfortable bandage.

The traditional wound covering does not permit close control over the temperature of the wound area. Prior art heated bandages which rely on a non-contact enclosure may use point source type heaters which result in variations in radiant heat flux depending on the location of the heater within the enclosure. Therefore there is a need for a non-contact bandage which can be used to control the environment of the wound and which may be reliably and comfortably attached to the skin.

SUMMARY

The wound treatment device 10 of the present invention has a planar upper surface displaced above the patient's skin surface, and an attachment surface generally in the plane of the patient's skin. Together these two surfaces define an enclosed non-contact volume over the wound treatment site.

The wound treatment device 10 may be divided into three separate parts for the purpose of description. These parts are an attachment portion 12, a wound treatment portion 14, and a transition portion 16. Each portion is designed to serve a separate function.

The attachment portion 12 is used to connect the wound treatment device 10 to the skin of a patient. The attachment portion 12 will usually be formed as an annular attachment rim. An adhesive will typically be placed on the attachment rim to couple the wound treatment device 10 to the patient. The attachment portion 12 lies near the patients skin and defines a so called first plane.

The wound treatment portion 14 of the wound treatment device 10 includes a standoff which rises above the patient's skin surface. The standoff defines the vertical extent or dimension of the wound treatment device 10 and thus defines the location of the second plane. The wound treatment portion 14 and standoff also define both a wound treatment volume 24 and a wound treatment area 26. The wound treatment volume 24 is located over the surface of the wound. The atmosphere in this wound treatment volume 24 can be controlled by the wound treatment device 10. The wound treatment area 26 is defined on the patient surface 18 under the wound treatment portion 14, and will typically be centered over the lesion or wound.

The transition portion 16 connects the attachment portion 12 to the wound treatment portion 14. This transition portion 16 improves the comfort and utility of the wound treatment device when the patient moves and stretches the wound treatment device 10. This stretching causes the total projected area of the wound treatment device 10 to increase and the shape of the wound treatment device 10 to change. In practice, the bulk of the patient motion is accommodated by the compliance of the transition portion 16. As a consequence, the transition portion projected area 17 increases. The standoff of wound treatment portion 14 rests gently on the patient's skin and it may twist to accommodate patient motion. However since the standoff can slide along the patient's skin there is no substantial change in the projected wound treatment area 28 due to patient motion. During patient motion the attachment portion 12 remains affixed to the surface of the patient and is easily deformed by body motion because of its relatively small area. Consequently the attachment portion projected area 40 may undergo a slight increase in area as the attachment portion 12 moves with the underlying skin. Throughout this motion the second planar surface is supported above the patients skin surface and can be used to support a detachable heater 32 which can heat the wound surface. A switch may also be provided to reduce power supplied to the wound treatment device 10 if the device is crushed in to contact with the wound.

BRIEF DESCRIPTION OF THE DRAWINGS

The various figures of the drawing depict illustrative and exemplary forms of the wound treatment device 10. Throughout the several views, identical reference characters represent similar structures wherein:

FIG. 8 is an electrical schematic of a pressure sensitive switch for a heater system;

FIG. 9A is an exploded view of a pressure sensitive switch incorporated into a wound treatment device;

FIG. 9B is a view of a portion of the pressure sensitive switch;

FIG. 10 is a perspective view of a passive heater embodiment of the wound treatment device;

DETAILED DESCRIPTION

Figure 1:
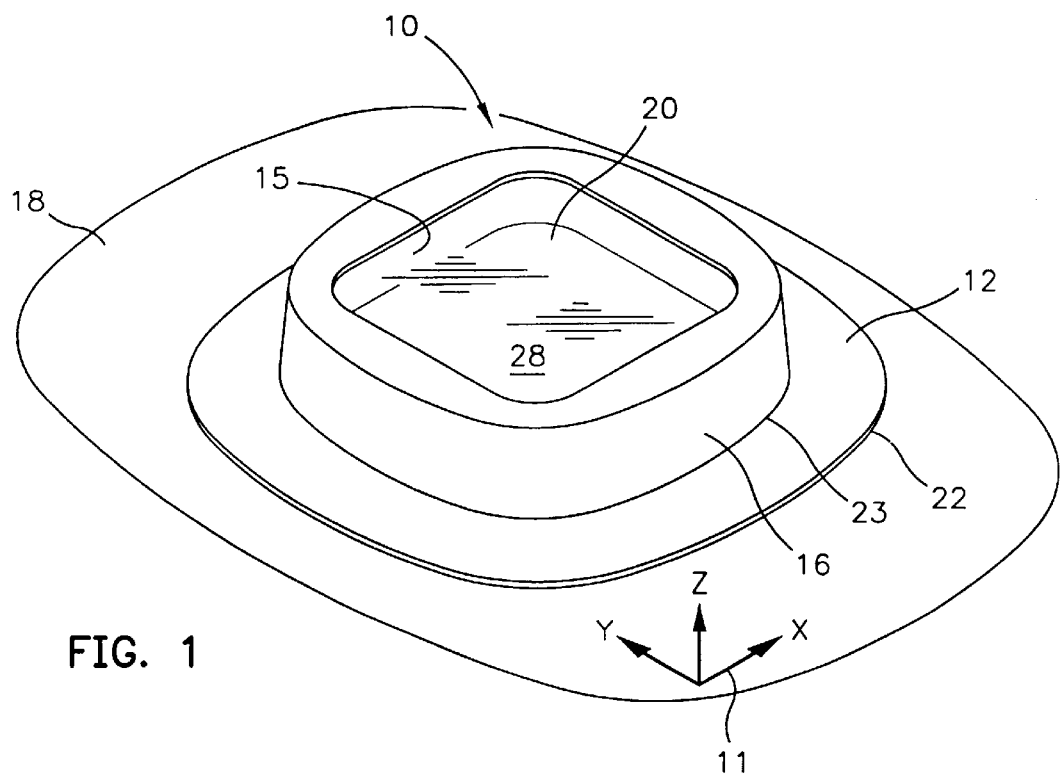
FIG. 1 is a perspective view of a first embodiment of the wound treatment device.

FIG. 1 is a perspective view of the wound treatment device 10 applied to a patient's skin surface 18. A coordinate system 11 is depicted on the patient's skin surface 18 and it defines X,Y and Z directions. The attachment portion 12 is formed as an planar rim or flange. This element is attached to the patient's skin with an adhesive and it lies in a first XY plane. In this first embodiment of the wound treatment device 10 the transition portion 16 is integrally formed with the attachment portion 12. The transition portion 16 rises vertically from the skin surface in the Z direction to connect to the wound treatment portion 14. In this embodiment the wound treatment portion 14 has a transparent wound cover 20 which allows one to see the wound treatment area 28. The wound cover 20 is supported above the first XY plane by a foam ring standoff 15. The wound cover 20 lies in a second XY plane that is vertically displaced along the Z-axis by the foam ring standoff 15 from the first XY plane. The wound cover 20 and foam ring standoff 15 together form the wound treatment portion 14. The region over the wound treatment area 28 is called the wound treatment volume 24.

In this figure the wound treatment device 10 has been applied to a patient's skin and is in a relaxed state. In this unstressed state one can see the outer periphery 22 of the attachment portion 12. The inner periphery 23 is shown by a crease in the structure where it connects to the transition portion 16.

Figure 2:
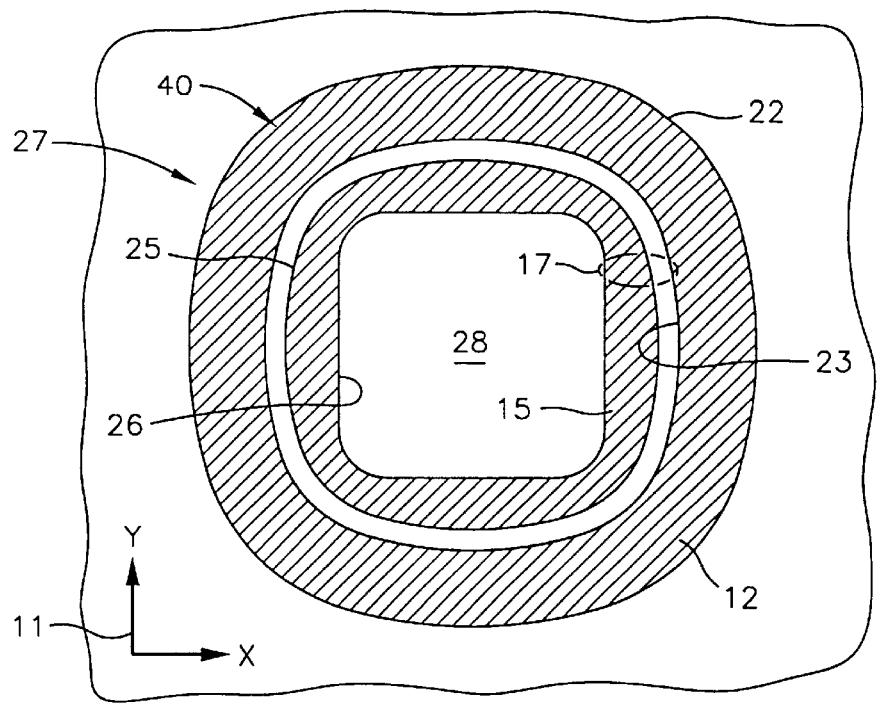
FIG. 2 is a schematic view of projected areas.
Figure 3:
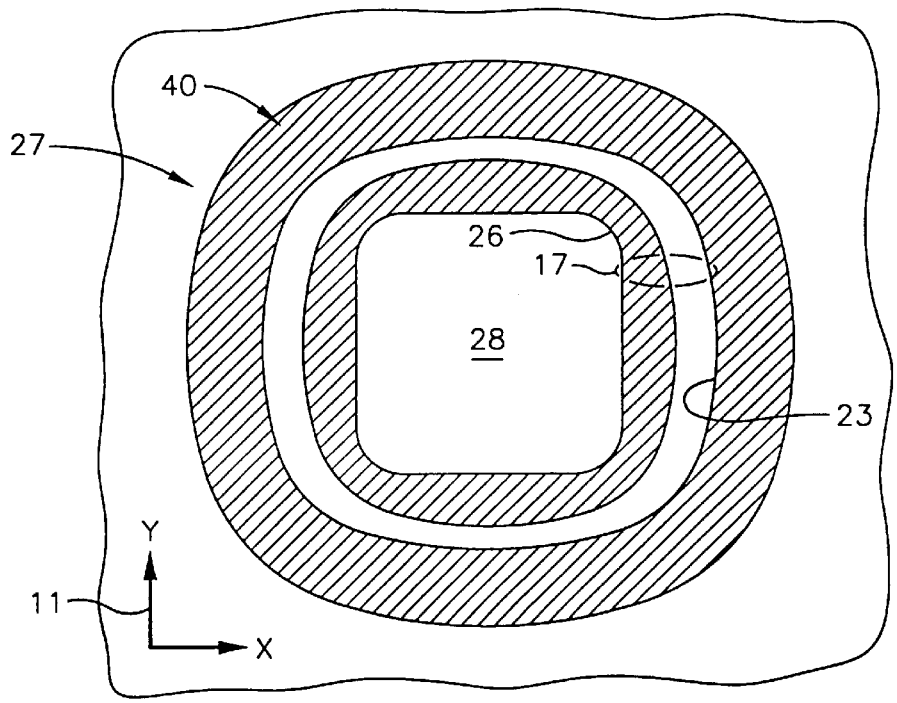
FIG. 3 is a schematic view of projected areas

FIG. 2 and FIG. 3 should be considered together. Together they show the influence of patient motion on the wound treatment device 10. Both FIG. 2 and FIG. 3 are top views of the wound treatment device 10 of FIG. 1 with the various portions of the wound treatment device 10 projected onto the first XY plane.

In FIG. 2 the wound covering is shown in a relaxed and unstretched state having a nominal total projected area 27. The projected wound treatment area 28 is shown at the center of the wound treatment device 10. The outline of the foam ring standoff 15 may be seen as the crosshatch area bounded by exterior perimeter 25 of the foam ring standoff 15, and the interior perimeter 26 of the foam ring standoff 15. The transition portion projected area 17 is shown in the figure bounded by the inner periphery 23 of the attachment portion 12, and the interior perimeter 26 of the foam ring standoff 15. The attachment portion projected area 40 is shown as the cross hatched area bounded by the outer periphery 22 and the inner periphery 23 of the attachment portion 12.

FIG. 3 shows the wound treatment device 10 stretched along the X-axis by patient motion. In comparison to FIG. 2 the overall or total projected area 27 of the wound treatment device 10 has increased. The attachment portion projected area 40 has increased slightly as the attachment portion moves with the underlying skin. The projected wound enclosure area 28 is essentially unchanged in area since in this embodiment the foam ring standoff 15 is free move against the skin. The largest percentage area change occurs in the transition portion projected area 17. As the wound treatment device 10 deforms in response to patient motion the transition portion is compliant and pays out material permitting the majority of the total projected area 27 increase to be accommodated primarily by the transition portion projected area 17.

Figure 4:
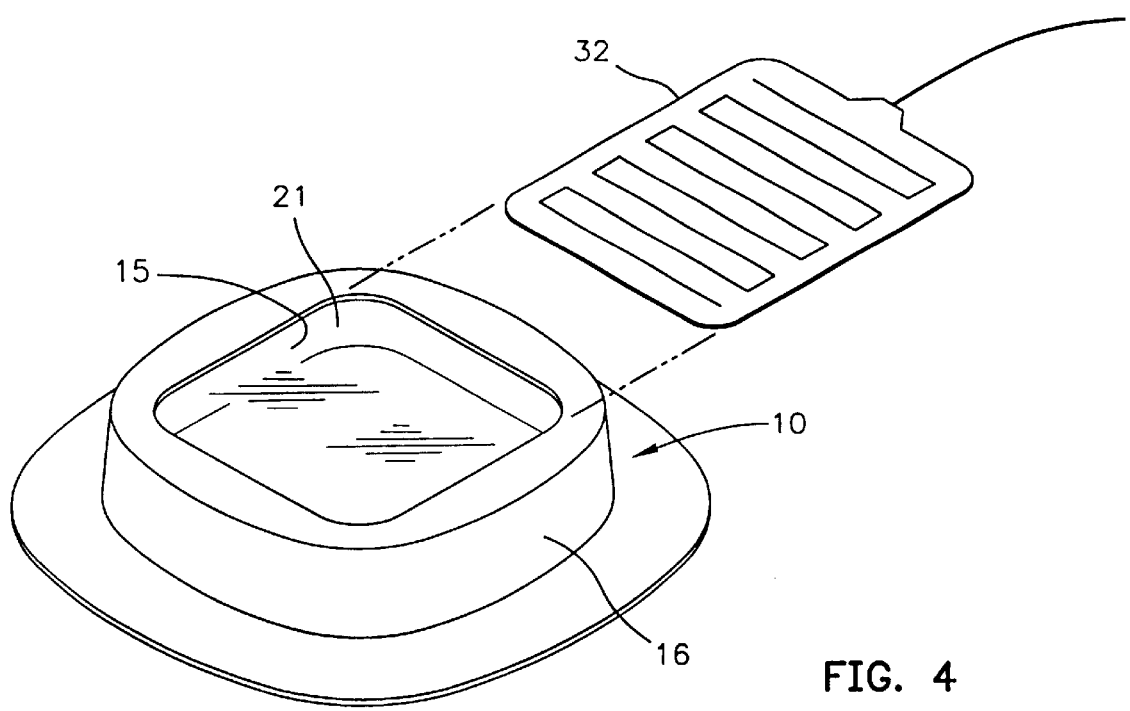
FIG. 4 is a perspective view of a detachable heater in combination with a first embodiment of the wound treatment device.

FIG. 4 shows a detachable heater 32 positioned for insertion into a pocket formed by pocket cover 21. Pocket cover 21 is bonded to the wound cover 20 and is sized to retain the heater 32. The foam ring standoff 15 and wound cover 20 serve to stabilize the shape of the wound treatment device while the transition portion accommodates patient motion. Consequently the heater is reliably and comfortably positioned above the wound surface. In general it is desirable to use a planar heater 32 which has a constant heat output per unit area. This form of heater results in a more uniform flux of radiant energy applied to the wound. And the amount of heat supplied to the wound area is largely independent of the height of the heater 32 above the wound surface.

Figure 5:
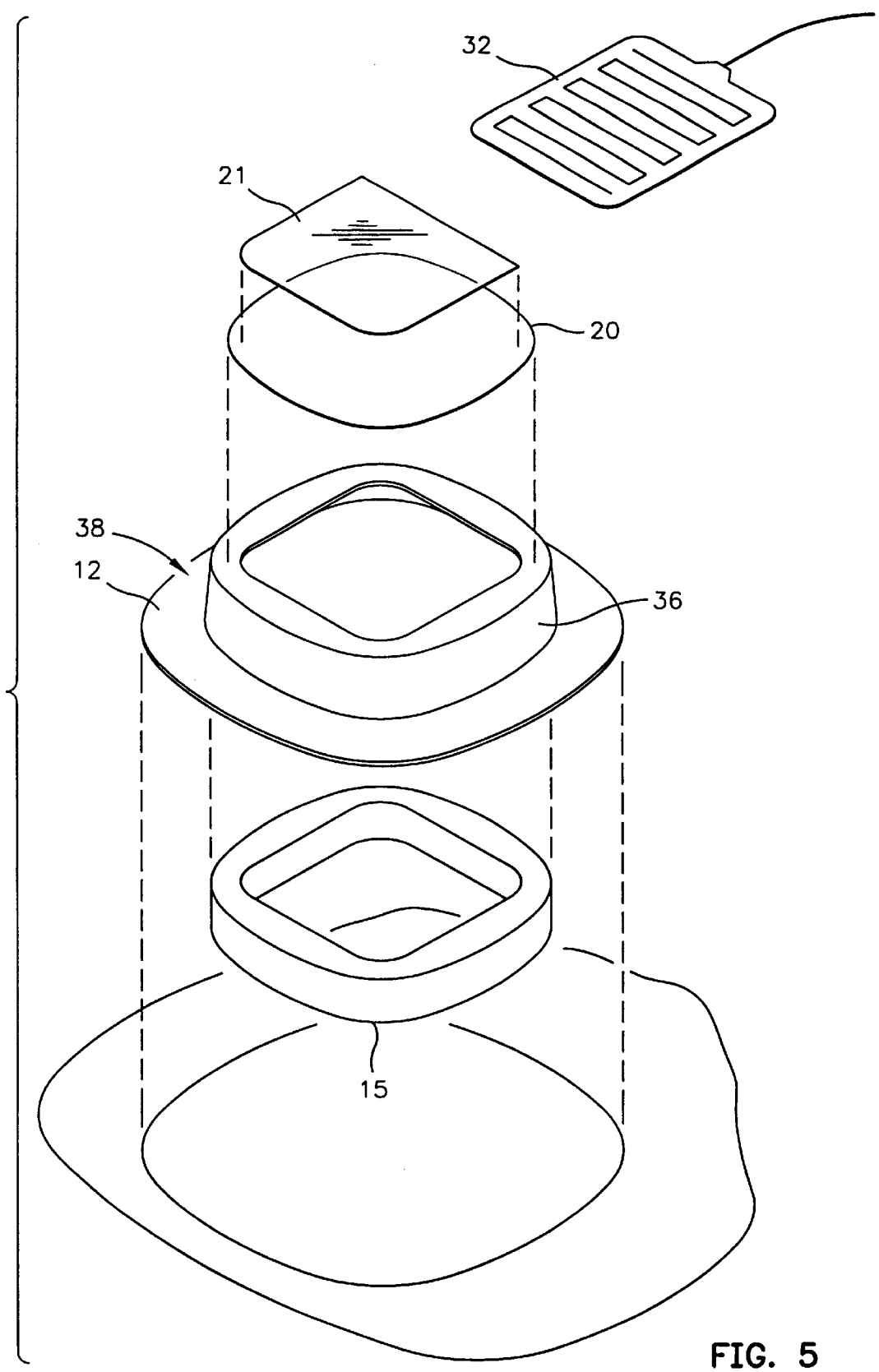
FIG. 5 is an exploded view of the first embodiment of the wound treatment device.

FIG. 5 is an exploded view of the first embodiment of the wound treatment device 10. The attachment portion 12 and transition portion membrane 36 are formed as a unitary composite shell 38. The composite shell may be vacuum formed from closed cell polyolefin foams such as Volara-6AS, which is a polyethylene material as sold by Illbruck Inc. of Minneapolis, Minn. It should be apparent that many other materials may be substituted within the scope of the invention. The foam ring standoff 15 may be die cut from foam sheeting of a reticulated polyurethane foam. The absorbency of the foam as well as its mechanical properties can be tailored to the particular wound treatment application. For example, the foam standoff may be impregnated with a medicament such as an antibiotic; antifungal; or antimicrobial material. It may also be desirable to supply a deodorant material or nitric oxide releasing material from the foam standoff. The wound cover 20 and wound pocket 21 may be made from a thin film of polyethylene. In general, the composite shell should be sufficiently self supporting so that when the wound treatment device 10 is removed from its release liner the wound treatment portion 14 is held up or supported by the shaped flexion joint of the transition portion membrane 36, and some effort is required to evert the composite shell and turn it inside out. This behavior defines the self supporting feature which causes the foam ring standoff 15 to lie gently against the skin even when the wound treatment device 10 is upside down. For larger wound coverings it may be desirable to apply a tacky adhesive to the patient contact surface of the standoff.

Figure 6:
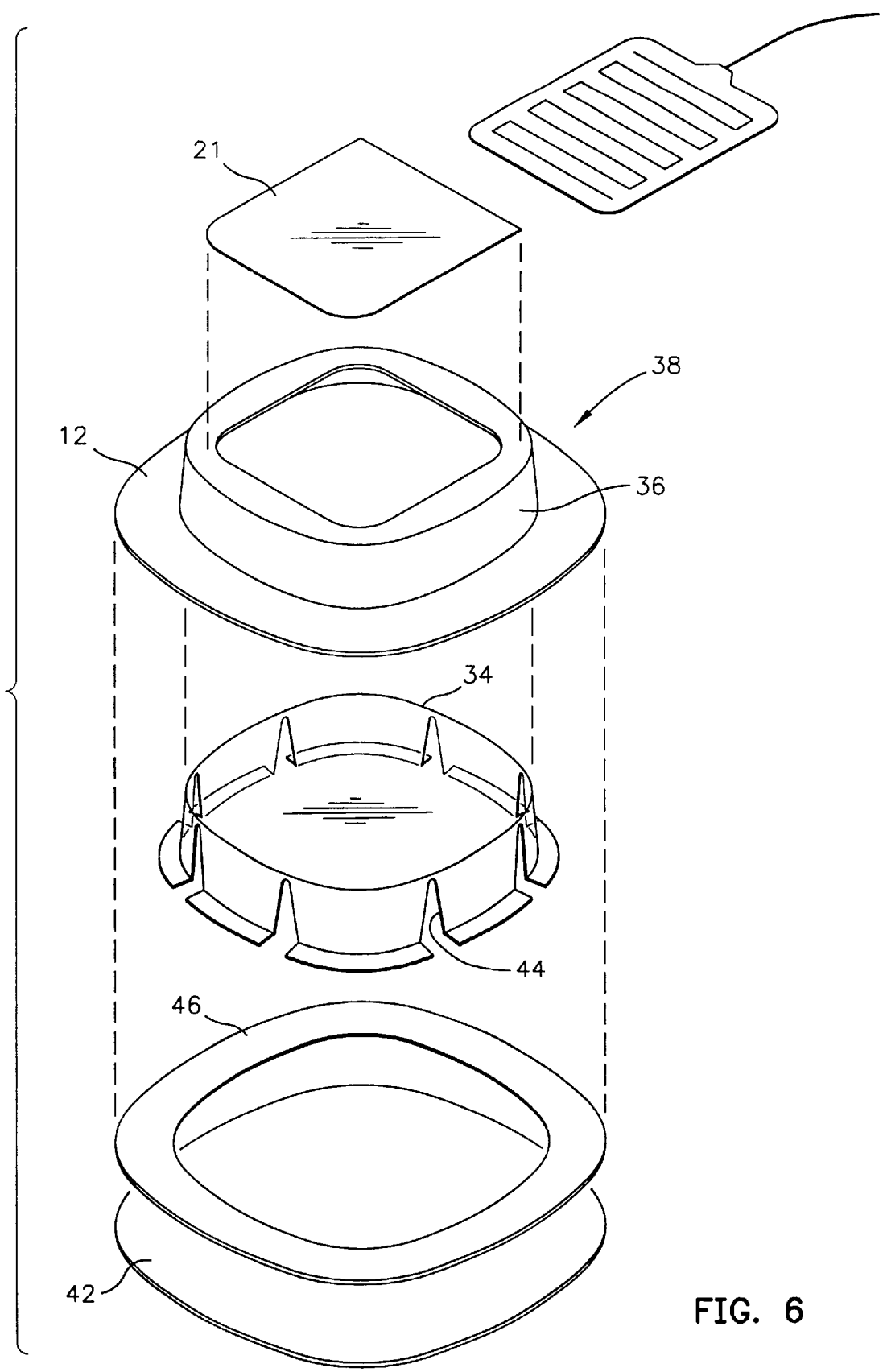
FIG. 6 is an exploded view of the second embodiment of the wound treatment device.

FIG. 6 is an exploded view of the second embodiment of the wound treatment device 10. The attachment portion 12 and transition portion membrane 36 are formed as a unitary composite shell 38. In this embodiment the wound treatment volume is formed by a serrated cup standoff 34. This member made be made from a more rigid polymeric material such as polyethylene or the like. The serrations typified by serration 44 permit the serrated cup to flex and accommodate patient motion. This embodiment shows a release liner 42 coupled to the attachment portion 12 of the composite shell 38 with an adhesive 46. In this embodiment the pocket cover 21 is bonded to the composite shell 38.

Figure 7:
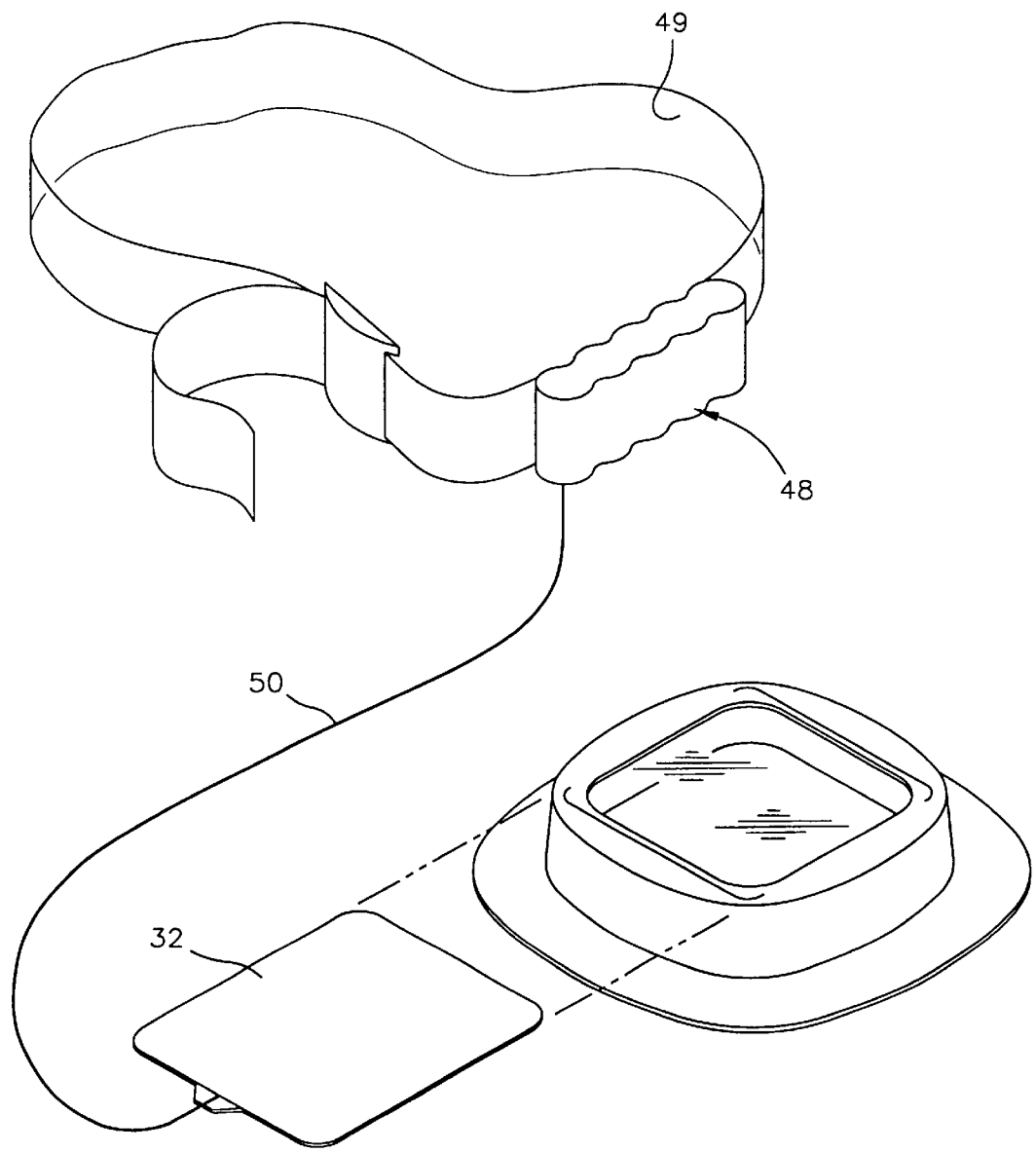
FIG. 7 is a perspective view of a heater system.

FIG. 7 depicts a power supply to permit the ambulatory use of the heated versions of the wound treatment device. A collection of battery cells may be wired together to form the power supply 48 which may be conveniently attached to a belt 49. A suitable cable 50 may be used to conduct power to the heater 32. In many instances it may be desirable to cut off power to the heater if the wound treatment device is collapsed against the wound to prevent overheating of the wound surface.

FIG. 8 shows a schematic representation of a touch switch which may be incorporated directly into the detachable heater 32. The heater 32 includes a continuous resistive heating coil 51. A conductive membrane 52 is arranged near the coil 51 so that it may "short out" segments or portions of the coil 51. In use power to the coil is completely turned off by pressure applied to the entire touch sensor 53.

FIG. 9A shows an exploded version of the heater 32 which incorporates a touch switch of the type described schematically in FIG. 8. The switch cover 45 has a conductive membrane which is located over the conductive pattern of the heating coil 51. It is held in position with an adhesive band 54. FIG. 9B shows the underside of the switch cover 45 showing a number of discrete insulation bumps typified by bump 47 which serve to space and support the conductive membrane 52 above the heating coil pattern 51. Pressure supplied to the switch cover inactivates the heater coil 51.

FIG. 10 shows a an accessory device 55 or cover. This may take the form of a passive heater with a reflective surface facing the wound. The accessory device may also take the form of a mapping grid where a grid work of lines is positioned on a transparent card to permit tacking of the wound healing process.

FIG. 11A through FIG. 11D should be considered together. These drawings facilitate a description of connection structures of the invention and represent several alternative connection geometries. In general to accommodate patient motion the transition portion pays out stored material to increase the projected area of the transition portion. Each of these drawings represents a mechanical schematic cross section of a wound treatment device 10 in the XZ plane. In each figure the wound covering is in the relaxed state.

Figure 11A:
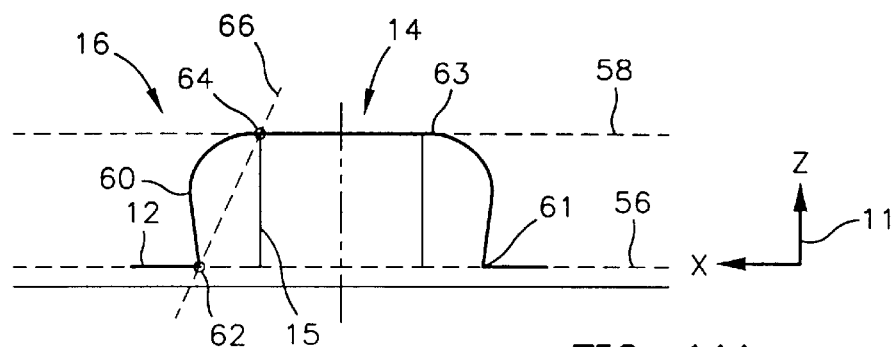
FIG. 11A is a schematic drawing depicting an alternate geometry for the transition portion.

FIG. 11A shows a schematic standoff 15 extending from a first plane 56 to a second plane 58. The transition portion 16 has a transition portion membrane 60 which is coupled to the attachment portion 12 by a first flexible connection 62 formed at the intersection of the attachment portion 12 and the transition portion 16. The transition portion membrane 60 is connected to the treatment portion at a second flexible connection 64 which is formed at the intersection of the transition portion 16 and the wound treatment portion 14. The wound treatment portion 14 is generally a cylindrical cup shaped structure defining a wound treatment area on the patient skin surface. The minimum interconnection distance 66 is depicted as a dashed line extending from the first flexible connection 62 to the second flexible connection 64. The length of this minimum interconnection distance 66 can be used to characterize the "-length" of the transition portion membrane 60. For many embodiments of the invention the length of the transition portion 16 between the first flexible connection 62 and the second flexible connection 64 is greater than the length of the straight line drawn between these points. This relationship is true for many embodiments of the wound treatment device when they are in the relaxed or unstressed position. It should be noted that the vertical distance between the first plane 56 and the second plane 58 represents a minimum value for the minimum interconnection distance 66. In the XY plane the first flexible connection 62 forms a first perimeter 61 and a second perimeter 63. In the embodiment depicted in FIG. 11A the first perimeter 61 is larger than the second perimeter 63.

Figure 11B:
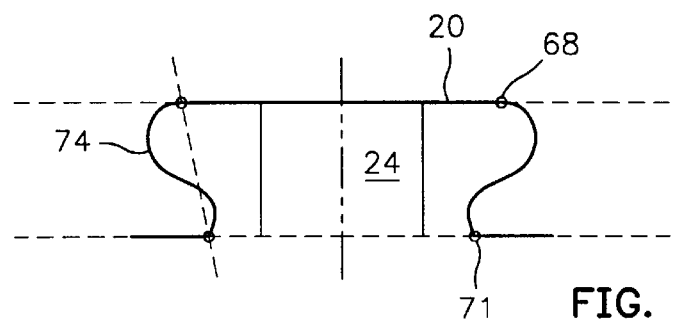
FIG. 11B is a schematic drawing depicting an alternate geometry for the transition portion.

FIG. 11B is a mechanical schematic diagram which represents a cross section of another embodiment of the wound treatment device 10 with an alternate connection geometry. In this drawing the wound cover 20 extends radially beyond the wound treatment volume 24 so that the second perimeter 68 is greater than the first perimeter 71. This generates a reflex transition portion 74 construction which may be adopted to increase the "length" and amount of material in the reflex transition portion 74.

Figure 11C:
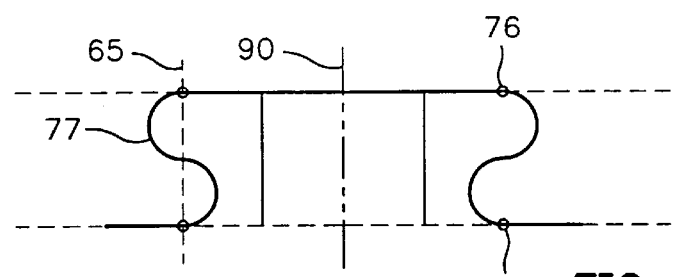
FIG. 11C is a schematic drawing depicting an alternate geometry for the transition portion.

FIG. 11C shows a construction where the first perimeter 76 and the second perimeter 78 have approximately the same value and are both concentric with the axis 90. This construction can produce an undulated transition portion 77. Once again the length of the undulated transition portion 77 exceeds the length of the line 65 between the first perimeter 78 and the second perimeter 76.

Figure 11D:
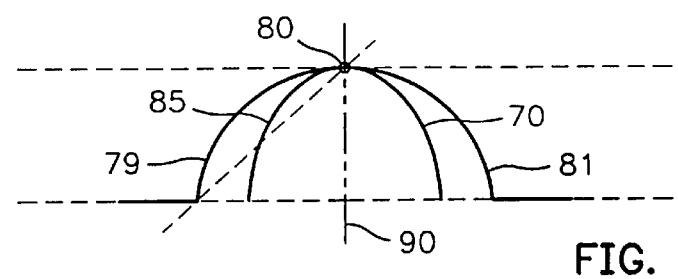
FIG. 11D is a schematic drawing depicting an alternate geometry for the transition portion.

FIG. 11D shows a hemispheric shell 70 as the wound treatment portion 14. In this embodiment the second perimeter 80 is a single attachment point generally concentric with the axis 90. In this embodiment the first perimeter 81 has a length which greatly exceeds the second perimeter 80 length. This construction forms a hemispheric transition portion 79 which has a length which exceeds the linear distance between the second perimeter 80 and the first perimeter 81 along the line 85.

Although the various geometries vary in detail it is preferred to form the transition portion from a resilient material which is generally self-supporting, yet sufficiently flexible so that it acts as a compliant hinge mechanism. This flexibility prevents the transfer of shearing force from the wound treatment portion 14 to the attachment portion 12 of the wound treatment device 10 and visa versa. With the geometries set forth in FIG. 11A through FIG. 11D the transition portion of the wound treatment device 10 forms a shaped flexion joint or formed expansion joint which stores "material" in a pleat, convolution or bellows or the like. This type of structure provides a means for expanding the size of the transition portion to minimize the transfer of forces from the attachment portion 12 to the wound treatment portion 14.

FIG. 12A through FIG. 14B should be considered together. In these embodiments of the invention the standoff structure reduces in height to result in the increased transition portion area during the stretching of the wound treatment device.

Figure 12A:
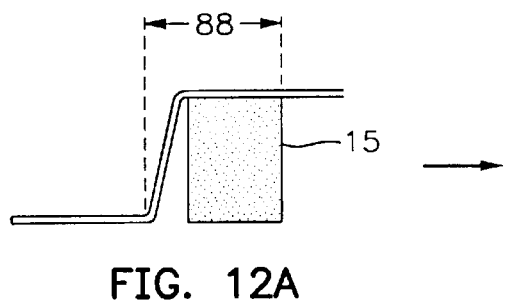
FIG. 12A is a schematic drawing depicting functional relationships between several elements of the invention.
Figure 12B:
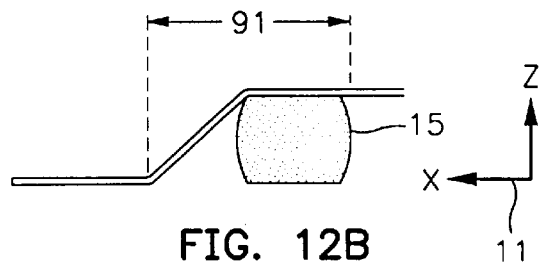
FIG. 12B is a schematic drawing depicting functional relationships between several elements of the invention.

FIG. 12A shows a part of a wound treatment device having a foam ring standoff 15 which is shown in the unstressed or relaxed state. In this instance the transition portion projected area 17 is proportional to dimension 88. In FIG. 12B the wound treatment device has been stretched and the height of the foam ring standoff 15 is reduced in the Z direction which has increased the transition portion projected area as represented by dimension 91.

Figure 13A:
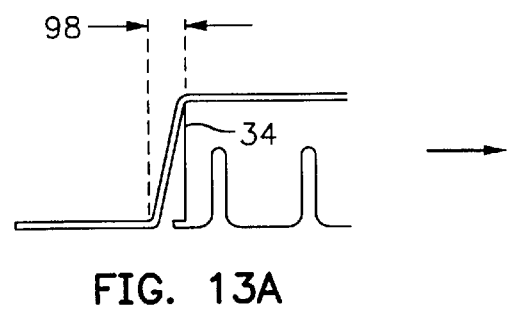
FIG. 13A is a schematic drawing depicting functional relationships between several elements of the invention.
Figure 13B:
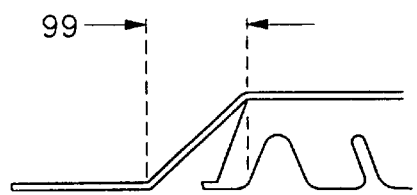
FIG. 13B is a schematic drawing depicting functional relationships between several elements of the invention.

FIG. 13A shows a part of a wound treatment device having a serrated cup standoff 34 which is shown in the unstressed or relaxed state. In this instance the transition portion projected area 17 is proportional to dimension 98. In FIG. 13B the wound treatment device has been stretched and the height of the serrated cup standoff 34 is reduced in the Z direction. The serrated wall sections splay out to permit the height reduction which has increased the transition portion projected area as represented by dimension 99.

Figure 14A:
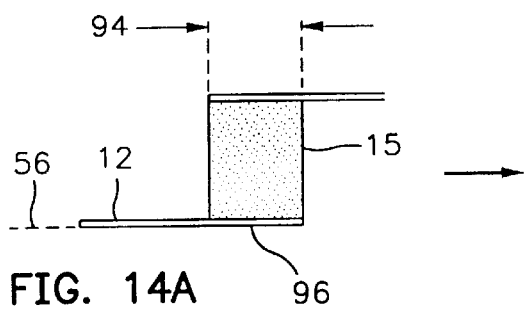
FIG. 14A is a schematic drawing depicting functional relationships between several elements of the invention.
Figure 14B:
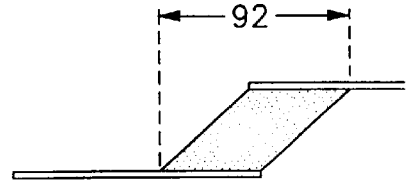
FIG. 14B is a schematic drawing depicting functional relationships between several elements of the invention.

FIG. 14A shows a part of a wound treatment device having a foam ring standoff 15 which is shown in the unstressed or relaxed state. However in this construction the attachment portion 12 and transition portion membrane 96 lie entirely in the first plane 56. In this instance the transition portion projected area 17 is proportional to dimension 94. In FIG. 14B the wound treatment device has been stretched and the height of the foam ring standoff 15 is reduced in the Z direction. This height reduction which has increased the transition portion projected area is represented by dimension 92.

Having thus described the invention it should be apparent that numerous changes may be made without departing from the scope of the invention as defined by the claims.

What is claimed is:

1. A wound treatment device, comprising:
   an attachment portion in a first plane;
   a wound treatment portion including a wound cover in a second plane for defining a wound treatment volume extending between the first plane and the second plane;
   a standoff acting between the attachment portion and the wound cover; and
   a flexible composite shell attached to the standoff and connecting the attachment portion to the wound treatment portion.

2. The wound treatment device of claim 1, wherein the wound cover is for supporting a heater over the wound treatment volume.

3. The wound treatment device of claim 1, wherein the standoff has a substantially annular configuration.

4. The wound treatment device of claim 1, wherein the standoff comprises a foam ring.

5. The wound treatment device of claim 1, further including a heater disposed on the wound treatment portion over the wound treatment volume.

6. The wound treatment device of claim 5, wherein the wound treatment portion includes a pocket, the heater being disposed in the pocket.

7. The wound treatment device of claim 6, wherein the heater has a substantially planar configuration.

8. The wound treatment device of claim 5, further including a power supply connected to the heater.

9. The wound treatment device of claim 5, wherein the heater is a passive heater including a reflective surface facing the wound treatment volume.

10. A wound treatment device, comprising:
    an attachment portion in a first plane;
    a wound treatment portion including a wound cover in a second plane for defining a wound treatment volume extending between the first plane and the second plane;
    an annular standoff acting between the attachment portion and the wound cover; and
    a flexible composite shell attached to the annular standoff and connecting the attachment portion to the wound treatment portion.

11. A wound treatment device, comprising:
    an attachment portion in a first plane;
    a wound treatment portion including a wound cover in a second plane for defining a wound treatment volume extending between the first plane and the second plane;
    a foam ring acting between the attachment portion and the wound cover; and
    a flexible composite shell attached to the foam ring and connecting the attachment portion to the wound treatment portion.

12. A wound treatment device, comprising:
    an attachment portion in a first plane;
    a wound treatment portion including a wound cover in a second plane for defining a wound treatment volume extending between the first plane and the second plane;
    a standoff acting between the attachment portion and the wound cover;
    a flexible composite shell attached to the standoff and connecting the attachment portion to the wound treatment portion; and
    a heater with a reflective surface disposed on the wound treatment portion such that the reflective surface faces the wound treatment volume.

\* \* \* \* \*